United States Patent
Blatt et al.

[11] Patent Number: 6,156,347
[45] Date of Patent: Dec. 5, 2000

[54] CONTROLLED RELEASE CHROMIUM PICOLINATE

[75] Inventors: Yoav Blatt, Rehovot; Oded Friedman, Holon; Eugene Kimelman, Yavne; Avner Rotman, Rehovot, all of Israel

[73] Assignee: Bio-Dar Ltd., Yavne, Israel

[21] Appl. No.: 09/010,165

[22] Filed: Jan. 21, 1998

[51] Int. Cl.[7] .................................................... A61K 9/22
[52] U.S. Cl. ..................... 424/497; 424/451; 424/454; 424/456; 424/461; 424/462; 424/463; 424/476; 424/479; 424/480; 424/482; 424/490
[58] Field of Search ................................. 424/682, 468, 424/464, 489, 195.1, 450, 43, 45, 480, 490, 497, 451, 456, 476, 479, 482, 463, 461, 462

[56] References Cited

U.S. PATENT DOCUMENTS

| | | |
|---|---|---|
| 4,315,927 | 2/1982 | Evans . |
| 4,898,734 | 2/1990 | Mathiowitz et al. . |
| 4,954,492 | 9/1990 | Jensen . |
| 5,013,752 | 5/1991 | Dobbins . |
| 5,087,623 | 2/1992 | Boynton et al. . |
| 5,366,990 | 11/1994 | Reid . |
| 5,550,113 | 8/1996 | Mann . |
| 5,603,961 | 2/1997 | Suzuki et al. . |
| 5,753,234 | 5/1998 | Lee et al. . |
| 5,798,101 | 8/1998 | Haveson .............................. 424/195.1 |
| 5,849,338 | 12/1998 | Richardson et al. ..................... 424/682 |
| 5,891,465 | 4/1999 | Keller et al. ............................ 424/450 |

*Primary Examiner*—Thurman K. Page
*Attorney, Agent, or Firm*—Darby & Darby

[57] ABSTRACT

The present invention relates to controlled/extended release oral dosage forms of chromium picolinate. Chromium picolinate is a common and effective biologically active form of chromium. As such, it has beneficial nutritional and therapeutic effects including improved insulin metabolism and lipid lowering activity.

The controlled dosage form of the present invention can be provided in various ways, including matrix formulations such as matrix tablets or multiparticulate formulations like micro capsules or coated pellets put into hard gelatin capsules. This provides effective drug delivery for extended periods of time, at relatively stable, optimal plasma peak values, with minimal undesirable side effects.

The invention provides effective controlled/extended release oral dosage formulations of chromium picolinate and processes for their preparation.

15 Claims, No Drawings

CONTROLLED RELEASE CHROMIUM PICOLINATE

FIELD OF THE INVENTION

The present invention relates to effective controlled/extended release formulations for therapeutic or nutritional administration of chromium picolinate and processes for their preparation.

Chromium picolinate is an exceptionally bioactive source of chromium. Consequently, it has a number of most significant beneficial effects, including improved insulin metabolism and body lipid control.

BACKGROUND OF THE INVENTION

Chromium picolinate is a biologically active form of chromium, chromium itself being an essential trace mineral needed for carbohydrate, protein and fat metabolism. It also plays an important role in insulin metabolism.

Numerous scientific publications describe Chromium picolinate's preparation, effects and applications. Among others, its general preparation, chemical and biological properties have been described by G. W. Evans and D. J. Pouchnik in J. Inorgan. Biochem., 49, 177 (1993), its clinical effect on insulin metabolism has been documented by G. W. Evans in Int. J. Biosocial Med. Res., 11, 163 (1989) and its lipid lowering activity has been reported by R. I. Press in West. J. Med., 152, 41 (1990).

These studies and many others, have established chromium's role as a nutritionally essential trace element. They have also demonstrated that chromium picolinate is a highly effective and convenient, dietary source for biologically available chromium. Its effect on proper insulin function, indicates that it can play an essential role in ameliorating risk of cardiovascular disease. Chromium has also been shown to be in dietary undersupply in large segments of various populations. Therefore insuring sufficient chromium availability by diet supplementation with chromium picolinate in appropriate, convenient and effective form, would appear to be a prudent health practice.

Consequently, it is an object of certain aspects of the present invention, to provide convenient controlled release oral dosage forms of chromium that supply in vivo optimum plasma biologically active and effective concentrations of chromium for extended periods of time.

It is another object of certain aspects of the present invention to provide an oral dosage form of chromium that minimizes risk of over dosage and undesirable side effects.

It is another object of certain aspects of the present invention to provide a dosage form of chromium that will supply prolonged and relatively constant bioavailable concentrations of chromium over extended periods of time.

It is another object of certain aspects of the present invention to provide an oral dosage form of chromium with optimum bioavailability of the chromium.

It is another object of certain aspects of the present invention to provide a convenient dosage form for chromium, that facilitates patient compliance with recommended procedures.

SUMMARY OF THE INVENTION

In accordance with this invention there is provided oral controlled/extended release dosage forms of chromium picolinate including matrix formulations such as matrix tablets, and multiparticulate formulations such as microcapsules or coated pellets embedded in hard gelatin capsules. The invention also provides processes for preparing such oral controlled/extended release dosage forms of chromium picolinate.

The in vitro dissolution time of such oral controlled/extended release dosage forms of chromium picolinate of the present invention, as determined according to USP XXI paddle method at 50 to 100 rpm, has been found to be between 6–24 hours for at least 80% of the chromium picolinate content, wherein the chromium picolinate content is between 1 to 80% on a weight/weight basis.

In one preferred formulation of the invention, spherical or irregular particles of chromium picolinate are coated with semi-permeable film comprising a mixture of water insoluble polymer such as ethyl cellulose and water soluble polymer such as hydroxypropylmethyl cellulose (HPMC) in a HPMC/Ethyl Cellulose ratio substantially within the range of 0.31 to 0.35.

Usually such polymer film coated active core particles exhibit a hyperbolic release pattern of active core through the polymer coating, over time. That is to say, the release of active ingredient, would diminish steeply with time. The specific polymer film coated particles produced in accordance with the present invention, provided a zero order, linear release profile. That is to say, the release of active ingredient from the active core of chromium picolinate when administered in this form, would be relatively constant over reasonably extended periods of time.

DETAILED DESCRIPTION OF THE INVENTION

The present invention relates to oral controlled/extended release dosage form of Chromium Picolinate applying either to matrix formulations such as matrix tablets or multiparticular formulations like micro capsules or coated pellets put into hard gelatin capsules. This is done in order to obtain a drug delivery system of Chromium Picolinate which will ensure a constant supply of the active ingredient during the day. By either embedding the Chromium Picolinate into a matrix formulation or incorporating it into a microcapsule formulation or both in order to control or extend the release, the following advantages are obtained compared to when conventional immediate release formulations are used:

A slower in vivo absorption of Chromium and hence optimal plasma peak values which hence reduce the occurrence of undesired side effects.

Prolonged and constant Chromium plasma concentrations over 24 hours which will avoid underdosing between dosage intervals.

A significant increase of the relative extent of Chromium bioavailability, i.e. the therapeutically relevant component.

Much higher tolerability of the drug, i.e. much less side effects A once daily dosing which together with the higher tolerability definitely will significantly increase the patient compliance.

Coating and Matrix Materials for Obtaining Controlled/Extended Release

In general, the formation of microencapsulated material and matrix adjuvant, is known in the art. As coating or matrix adjuvant, any coating or matrix material can be used. The type of material used will be chosen depending on the desired controlled release time-function, i.e., whether it will be a dosage form having a 6, 12, or 24 hours release time in vitro. The formulation of any specific and effective controlled release composition, will require careful adjustment and selection of the ingredients, in light of the results one needs to achieve.

Coating and matrix materials to be used are for instance:

Polymers:
  Synthetic polymers of polyvinyl type, e.g. poly vinylchloride, polyvinylacetate and copolymers thereof, polyvinylalcohol, polyvinylpyrrolidone.
  Polyethylene type, e.g. polyethylene, polystyrene.
  Polymers of acrylic acid or acrylic acid ester type, e.g. methylmetacrylate or copolymers of acrylic monomers.
  Biopolymers or modified biopolymers of cellulose, e.g. ethylcellulose, cellulose acetate phtalate, cellulose acetate, hydroxy propyl cellulose, hydroxypropylmethyl cellulose, methylcellulose, microcrystalline cellulose, Na-carboxymethyl cellulose. Shellac, Gelatin.
  Fats, oils, higher fatty acids and higher alcohols e.g. aluminium monostearate, cetylalcohol, hydrogenated beef tallow, hydrogenated castor oil, 12-hydroxystearyl alcohol, glyceryl mono- or dipalmitate, glyceryl mono- di- or tristearate, myristyl alcohol, stearic acid, stearyl alcohol. Polyethyleneglycols.
  Waxes e.g. beeswax, carnauba wax, Japan wax, paraffin, spermaceti, synthetic wax.
  Sugars and sugar alcohols e.g. mannitol, sorbitol, sucrose, xylitol, glucose, maltose.

The polymers mentioned above can be used depending on the technique applied as coating agents, matrix adjuvants or pharmaceutical binders. Whether the polymer will be a matrix adjuvant or a pharmaceutical binder will be dependent on the amount of polymer in the formulation.

Any combinations of the above mentioned polymers, fats and waxes can be used for encapsulation purposes as well as for matrix formation, viz. different polymers can be mixed, a polymer can be mixed with a fat or wax, etc.

The encapsulation of the drug can be achieved in the form of microcapsules, but the encapsulation is not restricted to the micro size.

The multiparticulate dosage forms, i.e., microcapsules or coated pellets as well as the matrix tablets useful for the present invention can be prepared by any of several acknowledged production processes including conventional granulation and tabletting of matrix tablets, pan coating, prilling, extrusion and spheronization, fluid bed processes, spray drying, spray chilling, coacervation and other processes.

Microcapsules or Coated Pellets

Microcapsules or coated pellets are defined as a solid or liquid core enclosed in a coating. The coating may also be referred to as the wall or shell. Various types of microcapsule structures can be obtained depending on the manufacturing process, e.g. mononuclear spherical, multinuclear spherical, multinuclear irregular, encapsulated mononuclear capsules, dual-walled microcapsules etc. Where no distinct coating and core region can be observed, the anologous terms are microparticles, microspheres, micromatrices, micro beads. The microcapsules or pellets usually have a particle size between 1 and 2000 microns.

The microcapsules or coated pellets of Chromium Picolinate can be filled into empty hard gelatine capsules to an extent corresponding to the desired dose or they can be gently compressed into a tablet by using suitable tablet excipients.

Chromium Picolinate could be mixed with a pharmaceutical binder to form micropellets which are then compressed into tablets.

The oral formulation of the invention could comprise micropellets which are then coated with a pharmaceutically acceptable coating adjuvant prior to being compressed into tablets.

The micropellets can also be filled into capsules.

The oral formulation of the invention could comprise microspheres which are then coated with a pharmaceutically acceptable coating adjuvant prior to being filled into capsules.

Maxtrix Formulations

Matrix formulations are defined as a drug embedded in insoluble excipients in order to achieve extended release by a continuous leaching of the drug from the inert matrix core. The release mechanism often follows the square root law of Higuchi. This term also applies to a matrix built of hydrophilic substances which in contact with water form a gel of high viscosity.

Preferred Embodiments

A preferred embodiment of the present invention is obtained when Chromium Picolinate is embedded in Hydroxypropyl methyl cellulose and then compressed into a tablet formulation using magnesium stearate as lubricant (round tablet, 6–8 mm in diameter).

Other preferred embodiments are obtained when Chromium Picolinate is embedded in polyvinyl chloride and ethyl cellulose by the addition of hydroxypropyl methyl cellulose, sodium carboxymethyl cellulose or paraffin. The material is then compressed into tablets using magnesium stearate as lubricant.

Still other preferred embodiments are when Chromium Picolinate is adsorbed on pellets made by extrusion or spheronization or any other way of sugar and/or a cellulose derivative e.g. microcrystalline. The microspheres are then coated with e.g. ethyl cellulose using a suitable plasticizer e.g. triethyl citrate. The microcapsules can be filled into empty hard gelatine capsules.

Other preferred embodiments are when Chromium Picolinate is suspended in a wax melt, e.g. carnauba wax, bees wax etc. and then spray chilled into microspheres. The spherical particles can then be coated with a fat or fatty acid, polyethylene glycol or a low melting wax by suspending the microspheres in the low melting excipient and then once again spray chill the slurry into microcapsules.

The invention will now be illustrated by the following non-limiting Examples.

EXAMPLE 1

Chromium Picolinate slow release was prepared by adsorbing the material on sugar beads using a binder and then coating the beads with a semipermeable membrane. 3 kg sugar beads, 25/30 mesh in size, were fluidized in a modified fluid bed coater (GPCG3, Glatt). The inlet temperature was adjusted to achieve a product temperature of 28° C. The beads were sprayed with a suspension of 136 g Chromium Picolinate (micronized particle size) and 272 g of hydroxy propyl methyl cellulose (Klucel, Hercules) in 1580 g of methanol. The speed of spraying the suspension was adjusted to obtain a high yield of adsorbed material on the beads and to prevent the formation of powder and agglomerates. At the end of the process the beads were sieved between 250 and 1000μ.

The adsorbed Chromium Picolinate beads were coated with a semipermeable membrane. This is done in order to slowly release the Chromium Picolinate into the medium. 4 kg of adsorbed beads were fluidized in a modified fluid bed coater (GPCG3, Glatt). The inlet temperature was adjusted to achieve a product temperature of 40° C. The beads were sprayed with a solution made according to the list below:

| | |
|---|---|
| Acetone | 720 g |
| Isoprepanol | 950 g |
| Ethyl cellulose | 145 g |
| Castor oil | 15 g |
| HPMC | 48 g |

The speed of spraying was adjusted in order to obtain a good and homogeneous film on the beads. The preparation was tested for its slow release properties by dissolution using a USP apparatus II (paddles), in 900 ml simulated intestinal fluid pH=7.2, 37° C. at 75 RPM. Samples were withdrawn at several time intervals and analyzed by HPLC for chromium Picolinate content.

The preparation released Chromium Picolinate to the medium slowly. Between 20 to 30% in 1 hour, between 30 to 45% in 2 hours, between 50 and 70% in 4 hours, more than 80% in 8 hours and more than 90% in 12 hours. The release pattern can be adjusted by varying the amount of the ethyl cellulose and HPMC in the coating solution.

EXAMPLE 2

Spherical or irregular active core particles of chromium picolinate were coated with films comprising mixtures of water insoluble polymer such as ethyl cellulose aand water soluble polymer such as hydroxypropylmethyl cellulose (HPMC). It was found that in most ratios of the two polymers, a hyperbolic release pattern of active core material by diffusion through the polymer film coating layer, was obtained. However, when the BPMC/Ethyl cellulose ratio was substantially in the range 0.31 to 0.35, a zero order, linear release profile was obtained.

While certain embodiments of the present invention have been particularly described, it will be apparent by persons skilled in the art that the present invention is not limited by the description and examples provided hereinbefore, and that many modifications and variations may be made that are all within the spirit and scope of the present invention. The invention is accordingly not to be construed as being restricted to such embodiments. Rather, its concepts, scope and spirit are to be understood having regard to the claims that follow.

What is claimed is:

1. A formulation for controlled/extended release of Chromium Picolinate characterized in that the total in vitro dissolution time determined according to USP XXI paddle method at 50 or 100 rpm is between 6–24 hours for at least 80% of the Chromium Picolinate content, said formulation comprising spherical or irregular particles of Chromium Picolinate coated with a mixed polymer film comprising a water soluble polymer and a water insoluble polymer in a ratio that produces a substantially zero order linear release pattern of active ingredient, wherein the Chromium Picolinate content is between 1 to 80% on a weight/weight basis.

2. A formulation according to claim 1 characterized in that it consists of Chromium Picolinate coated with an adjuvant selected from the group consisting of a synthetic polymer of the polyvinyl family, the polyethylene family, the cellulose family or the polyacrylate family, fats, waxes and sugar or combinations thereof.

3. A process for the preparation of an oral formulation, according to claim 1, characterized in that Chromium Picolinate is incorporated into a carrier which releases Chromium Picolinate in a total in vitro dissolution time, determined according to the USP XXI paddle method at 50 or 100 rpm, between 6 and 24 hours for at least 80 per cent of the Chromium Picolinate content.

4. The process according to claim 3 characterized in that Chromium Picolinate is coated with an adjuvant selected from the group consisting of a synthetic polymer of the polyvinyl type, the polyethylene type or the cellulose type, fats, waxes and sugars or combinations thereof and then either compressed into tablets or processed into microcapsules/pellets which are either filled into hard gelatin capsules or compressed into tablets.

5. A controlled/extended release formulation as in claim 1, wherein the water insoluble polymer is ethyl cellulose.

6. A controlled/extended release formulation as in claim 1, wherein the water soluble polymer is hydroxypropylmethyl cellulose (HPMC).

7. A controlled/extended release formulation as in claim 1, wherein the water insoluble polymer is ethyl cellulose and the water soluble polymer is hydroxypropylmethyl cellulose (HPMC) and wherein the HPMC/ethyl cellulose ratio is substantially between 0.31 to 0.35.

8. A formulation according to claim 1 characterized in that it consists of Chromium Picolinate coated with an adjuvant selected from the group consisting of a synthetic polymer of the polyvinyl family, the polyethylene family, the cellulose family or the polyacrylate family, fats, waxes and sugar or combinations thereof.

9. A formulation according to claim 3 characterized in that it consists of Chromium Picolinate coated with an adjuvant selected from the group consisting of a synthetic polymer of the polyvinyl family, the polyethylene family, the cellulose family or the polyacrylate family, fats, waxes and sugar or combinations thereof.

10. A formulation according to claim 1 in the form of a tablet containing Chromium Picolinate embedded in polyvinyl chloride and polyvinyl acetate and magnesium stearate as lubricant.

11. A formulation according to claim 10 in the form of a tablet containing Chromium Picolinate embedded in polyvinyl chloride and polyvinyl acetate and magnesium stearate as lubricant.

12. A formulation according to claim 11 in the form of a tablet containing Chromium Picolinate embedded in polyvinyl chloride and polyvinyl acetate and magnesium stearate as lubricant.

13. A process for the preparation of an oral formulation, according to claim 2, characterized in that Chromium Picolinate is incorporated into a carrier which releases Chromium Picolinate in a total in vitro dissolution time, determined according to the USP XXI paddle method at 50 or 100 rpm, between 6 and 24 hours for at least 80 per cent of the Chromium Picolinate content.

14. A process for producing a controlled/extended release formulation of Chromium Picolinate as in claim 6 by coating Chromium Picolinate containing particles with a mixed polymer film comprising ethyl cellulose and hydroxypropylmethyl cellulose (HPMC) wherein the HPMC/ethyl cellulose ratio is substantially between 0.31 to 0.35.

15. A process for producing a controlled/extended release formulation of Chromium Picolinate as in claim 7 by coating Chromium Picolinate containing particles with a mixed polymer film comprising ethyl cellulose and hydroxypropylmethyl cellulose (HPMC) wherein the HPMC/ethyl cellulose ratio is substantially between 0.31 to 0.35.

* * * * *